United States Patent [19]

Chandraratna

[11] Patent Number: 4,923,884
[45] Date of Patent: May 8, 1990

[54] ETHYNYLHETEROAROMATIC-ACIDS HAVING RETINOIC ACID-LIKE ACTIVITY

[75] Inventor: Roshantha A. S. Chandraratna, El Toro, Calif.

[73] Assignee: Allergan, Inc., Irvine, Calif.

[21] Appl. No.: 180,649

[22] Filed: Apr. 1, 1988

Related U.S. Application Data

[63] Continuation of Ser. No. 946,749, Dec. 24, 1986, abandoned.

[51] Int. Cl.⁵ .............. A61K 31/455; A61K 31/44; C07D 213/56; C07D 213/46
[52] U.S. Cl. ............................ 514/354; 514/355; 514/356; 514/357; 514/277; 514/247; 514/255; 514/269; 514/438; 514/448; 514/461; 514/471; 546/337; 546/340; 546/342; 546/344; 546/350; 549/70; 549/71; 549/72; 549/78; 549/484; 549/486; 549/487; 549/497; 549/505; 544/238; 544/242; 544/335; 544/336
[58] Field of Search ............ 546/337, 340, 342, 344, 546/350; 514/355, 356, 357, 277, 354

[56] References Cited

FOREIGN PATENT DOCUMENTS 0173172 3/1986 European Pat. Off. ............ 546/340

Primary Examiner—Mary C. Lee
Assistant Examiner—Johann Richter
Attorney, Agent, or Firm—James A. Kanagy; Stuart R. Suter

[57] ABSTRACT

Retinoid-like activity is exhibited by compounds of the formula

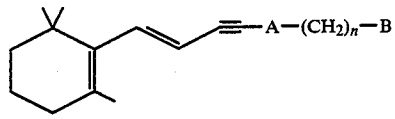

wherein A is pyridyl, furyl, thienyl, pyridazinyl, pyrimidinyl or pyrazinyl; n is 0–5; and B is H, —COOH and its esters, amides and pharmaceutically acceptable salts, —CHO and its acetal derivatives, —COR₁ and its ketal derivatives where R₁ is —(CH₂)ₙCH₃ where n is defined above, or —CH₂OH and its ether and acyl ester derivatives; or a pharmaceutically acceptable salt.

5 Claims, No Drawings

ETHYNYLHETEROAROMATIC-ACIDS HAVING RETINOIC ACID-LIKE ACTIVITY

This is a continuation of application Ser. No. 946,749, filed Dec. 24, 1986, now abandoned.

BACKGROUND

This invention relates to novel compounds having retinoid-like activity. More specifically, the invention relates to compounds wherein three olefinic units from the acid-containing end unit in retinoic acid are replaced by an ethynylheteroaromatic-containing functionality. Such modifications to the retinoic acid structure have retinoid acid-like activity.

RELATED ART

Nematocidal compounds disclosed in Japanese patent 56-123903, have the structure 2-(2-((1,1-dimethyl)-dimethylsilyl)oxy)ethyl-alpha-(4-(2,6,6-trimethyl-1-cyclohexene-1-yl)-3-buten-1-ynyl)-1-cyclopentene-1-methanol. This compound employees the 1-(2',6',6'-trimethyl-cyclohex-1'-enyl)-but-1-ene-3-yne moiety of the compounds disclosed herein. That fragment, however, is the only similarity between the Japanese disclosure and those recited herein. Such compounds are not dispositive of the instant invention.

SUMMARY OF THE INVENTION

This invention comprises compounds of formula I

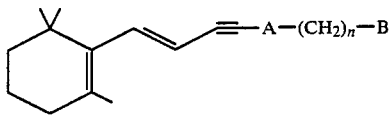

wherein A is pyridyl, furyl, thienyl, pyridazinyl, pyrimidinyl or pyrazinyl; n is 0–5; and B is H, —COOH and its esters, amides and pharmaceutically acceptable salts, —CHO and its acetal derivatives, —COR$_1$ and its ketal derivatives where R$_1$ is —(CH$_2$)$_n$CH$_3$ where n is defined above, or —CH$_2$OH and its ether and acyl ester derivatives; or a pharmaceutically acceptable salt.

In a second aspect, this invention relates to the use of the compounds of formula I for treating dermatoses, such as acne, Darier's disease, psoriasis, icthyosis, eczema, atopic dermatitis and epithelial cancers. These compounds are also useful in the treatment of arthritic diseases and other immunological disorders (e.g., lupus erythematosus), in promoting wound healing and in treating the dry eye syndrome.

This invention also relates to a pharmaceutical formulation comprising a compound of formula I in admixture with a pharmaceutically acceptable excipient.

In another aspect, this invention relates to the process for making a compound of formula I which process comprises reacting a compound of formula II with a compound of formula III in the presence of Pd(PQ$_3$)$_4$ (Q is phenyl) or a similar complex

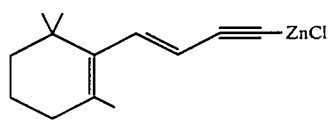

-continued
$$X—A—(CH_2)_n—B \qquad III$$

where X is a halogen, preferably I; A is pyridyl, furyl, thienyl, pyridazinyl, pyrimidinyl or pyrazinyl; n is the same as defined above; and B is H, or a protected acid, alcohol, aldehyde or ketone giving a compound corresponding to formula I; or homologating a compound of the formula

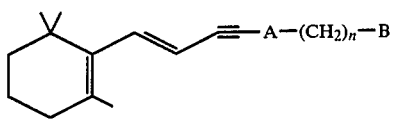

where n is 0–4 and A is a heterocycle as defined above; or
converting an acid of formula I to an acid or acid salt; or
converting an acid of formula I to an ester; or
converting an acid of formula I to an amide; or
reducing an acid to an alcohol or aldehyde; or
converting an alcohol to an ether or ester; or
oxidizing an alcohol to an aldehyde; or
converting an aldehyde to an acetal; or
converting a ketone to a ketal.

GENERAL EMBODIMENTS

Definitions

The term "ester" as used here refers to and covers any compound falling within the definition of that term as classically used in organic chemistry. It includes organic and inorganic esters. Where B is —COOH, this term covers the products derived from treatment of this function with alcohols or thioalcohols. Where the ester is derived from compounds where B is —CH$_2$OH, this term covers compounds derived from organic acids capable of forming esters such as phosphorous-based and sulfur-based acids, or compounds of the formula —CH$_2$OCOR where R is any substituted or unsubstituted aliphatic, aromatic, heteroaromatic or aliphatic-aromatic group.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Here, and where ever else used, lower alkyl means having 1–6 carbon atoms. Also preferred are the phenyl or lower alkylphenyl esters.

Amides has the meaning classically accorded that term in organic chemistry. In this instance it includes the unsubstituted amides and all aliphatic and aromatic mono- and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and di-substituted amides derived from the substituted and unsubstituted phenyl or lower alkylphenyl amines. Unsubstituted amides are also preferred.

Acetals and ketals includes the radicals of the formula —CK where K is (—OR)$_2$. Here, R is lower alkyl. Also, K may be —OR₁O— where $R_1$ is lower alkyl of 2–5 carbon atoms, straight chain or branched.

A pharmaceutically acceptable salt may be prepared for any compounds in this invention having a functionality capable of forming such salt, for example an acid or an amine functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic acids or bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

The preferred compounds of this invention are those where the ethynyl group and the B group are attached to the 2 and 5 positions respectively of a pyridine ring (the 6 and 3 positions in the nicotinic acid nomenclature being equivalent to the 2/5 designation in the pyridine nomenclature) or the 5 and 2 positions respectively of a thiophene group respectively; n is 0, 1 or 2; and B is —COOH, an alkali metal salt or organic amine salt, or a lower alkyl ester, or —CH₂OH and the lower alkyl esters thereof. The more preferred compounds are:

ethyl 6-[4'-(2",6",6"-trimethylcyclohex-1"-enyl)-but-3'-en-1'-ynyl]nicotinoate;

6-[4'-(2",6",6"-trimethylcyclohex-1"-enyl)-but-3'-en-1'-ynyl]nicotinic acid;

ethyl 5-[4'-(2",6",6"-trimethylcyclohex-1"-enyl)-but-3'-en-1'-ynyl]thiophene-2-carboxylate; and 5-[4'-(2",6",6"-trimethylcyclohex-1"-enyl)-but-3'-en-1'-ynyl]thiophene-2-carboxylic acid.

The compounds of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic acne, oral administration may also be used.

Any common topical formulation such as a solution, suspension, gel, ointment, or salve and the like may be used for topical treatment. Preparation of such topical formulations are well known and fully described in the art of pharmaceutical formulations as exemplified by, for example, *Remington's Pharmaceutical Science*, Edition 17, Mack Publishing Company, Easton, Pa. For topical application, these compounds could also be administered as a powder or spray, particularly in aerosol form.

If the drug is to be administered systemically, it may be confected as a powder, pill, tablet or the like, or as a syrup or elixir for oral administration. For intravenous or intraperitoneal administration, the compound will be prepared as a solution or suspension capable of being administered by injection. In certain cases, it may be useful to formulate these compounds in suppository form or as a sustained release formulation for deposit under the skin or intramuscular injection.

Other medicaments can be added to topical formulation for such secondary purposes as treating skin dryness, providing protection against light; other medications for treating dermatoses, preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the drug potentially could be used in a prophylactic manner to prevent onset of a particular condition. A given therapeutic concentration will vary from condition to condition and in certain instances may vary with the severity of the condition being treated and the patient's susceptibility to treatment. Accordingly, a given therapeutic concentration will be best determined at the time and place through routine experimentation.

It is anticipated that in the treatment of, for example, acne, or other such dermatoses, that a formulation containing between 0.01 and 1.0 milligrams per milliter of formulation will constitute a therapeutically effective concentration. If administered systemically, an amount between 0.01 and 5 mg per kg per day of body weight would be expected to effect a therapeutic result.

The retinoic acid like activity of these compounds was confirmed through the classic measure of retinoic acid activity involving the effects of retinoic acid on ornithine decarboxylase. The original work on the correlation between retinoic acid and decrease in cell proliferation was done by Verma & Boutwell, *Cancer Research*, 1977, 37, 2196–2201. That refernce discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although the causes for ODC activity increase are unknown, it is known that 12-O-tetradecanoylphorbol-13-acetate (TPA) induces ODC activity. Retinoic acid inhibits this induction of ODC activity by TPA. The compounds of this invention also inhibit TPA induction of ODC as demonstrated by an assay essentially following the procedure set out in *Cancer Res.*: 1662–1670, 1975.

Specific Embodiments

It is anticipated that the compounds of this invention can be made by a number of different synthetic chemical pathways. To illustrate this invention, a series of steps which have been used to obtain certain representative compounds of formula I are outlined in scheme I. The synthetic chemist will readily appreciate that the conditions set out in this writing are specific embodiments which can be generalized to any and all of the compounds represented by formula I.

Reaction Scheme I outlines the general procedure for making the compounds of formula I.

Scheme I

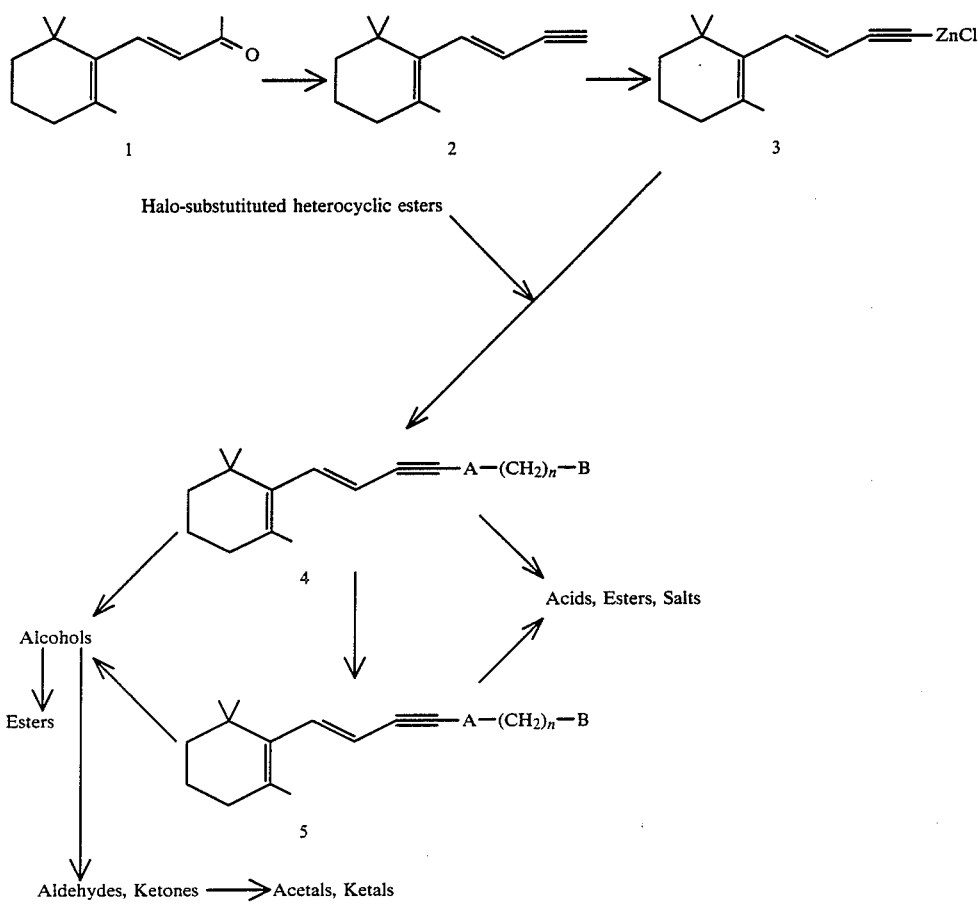

In this scheme, X may be Br, Cl or I, but Br and I are preferred. A and B and n have the same meaning as recited fir these identifiers on page 2 under the definition of the substituents of Formula I.

Stated generally, the acetylenic function is introduced by treating the ketone of formula I with a strong base and a dialkyl chlorophosphate followed by base treatment again. Then, by converting the acetylenic group to a heavy metal salt, the ZnCl salt, addition of the acetylenic function to an aromatic ring can be effected. Because of the basic nature of this ZnCl salt, the acidic properties of the B group must be minimized. Derivatizing acids, alcohols, aldehydes and ketone is necessary for optimizing reaction yields. Where it is necessary to extent the alkyl chain (—CH$_2$)$_n$—) after the preceeding step, that can be accomplished by an homologation reaction such as the Arndt-Eistert reaction.

The compound of formula I is sold by Aldrich Chemical Company under the name Beta-Ionone. The ketone is converted to a triple bond at reduced temperature under an inert atmosphere by means of lithium diisopropylamide (LDA) or a similar base. The reaction is carried out in an ether-type solvent such as a dialkyl ether or a cyclic ether, for example, tetrahydrofuran, pyran or the like.

More specifically, lithium diisopropylamide is generated in situ by mixing diisopropylamine in a dry solvent such as tetrahydrofuran, which is then cooled, to between −70° and −50° C. under an inert atmosphere. An equimolar amount of an alkyllithium compound such as n-butyl lithium in an appropriate solvent is then added at the reduced temperature and mixed for an appropriate time to permit formation of lithium diisopropylamide (LDA). The ketone of formula 1 (at least a 10% molar excess) is dissolved in the reaction solvent, the solution cooled to that of the LDA mixture, and added to that solution. After brief mixing, the solution is then treated with a dialkyl chlorophosphate, preferably diethyl chlorophosphate in about a 20% molar excess. The reaction solution is then gradually brought to room temperature. This solution is then added to a second lithium diisopropylamide solution which is prepared in situ using dry solvent and under an inert atmosphere, preferrably argon, at reduced temperature (−78° C.). Thereafter, the reaction mixture is again warmed to room temperature where it is stirred for an extended period of time, preferably between 10 and 20 hours, most preferably about 15 hours. The solution is then acidified and the product recovered by conventional separatory means.

The formula 3 compound is prepared under conditions which exclude all water and oxygen. A dry, ether-type solvent such as a dialkyl ether or a cyclic ether such as a furan or pyran, particularly tetrahydrofuran, may be used as the solvent. A solution of formula 2 is first prepared under an inert atmosphere such as argon or nitrogen, and then a strong base such as n-butyl lithium is added (in about a 10% molar excess). This reaction is begun at a reduced temperature of between −10° and +10° C., preferably about 0° C. The reaction mixture is stirred for a short period, between 30 minutes and 2 hours, and then treated with about a 10% molar excess of fused zinc chloride dissolved in the reaction solvent. This mixture is stirred for an additional 1-3 hours at about the starting temperature, then the temperature is increased to about ambient temperature for 10-40 minutes.

The halo-substituted heterocyclic esters are prepared from their corresponding acids, the halogen being Cl, Br or I. These pyridyl, furyl, thienyl and diazinyl acids are all available from chemical manufacturers or can be prepared by published methods. Esterification is effected by refluxing the acid in a solution of the appropriate alcohol in the presence of thionyl chloride or by reacting the acid and alcohol in the presence of dicyclohexylcarbodiimide and dimethylaminopyridine. The ester is recovered and purified by conventional means. Other conventional methods can also be used to effect esterification.

To effect formation of formula 4, the alkyl halofuranoate, or a corresponding alkyl halo ester of thiophene, pyridine or the several diazine isomers, is dissolved in a dry solvent. The ester is used in an amount approximating the molar quantity of the starting quantity of compound 3. This solution is introduced into a suspension of tetrakis(triphenylphosphine)palladium (about a 5 to 10% molar amount relative to the reactants) in the reaction solvent at a temperature of between about −10° and +10° C. This mixture is stirred briefly, for about 15 minutes. To this just prepared mixture is then added the pre-prepared solution of the compound 3, the zinc chloride salt, the addition being made at about room temperature. This solution is stirred for an extended period, between about 15 and 25 hours, at room temperature. The reaction is then quenched with acid and the product separated and purified by conventional means to give the compounds of formula 4.

Taking the esters of formula 4, saponifying them, and taking the resulting acids and subjecting them to successive Arndt-Eistert homologations gives those compounds of formula 5 where n is 1-5. These acids can then be converted to esters of formula I by the procedure outlined above for esterifying the halo-substituted heterocyclic acids.

Amide may be formed by any appropriate amidation means known in the art. In this instance, one way to prepare such compounds is to first make the acid chloride and then treat that compound with ammonium hydroxide. For example, the ester is treated with an alcoholic base such as ethanolic KOH (in approximately a 10% molar excess) at room temperature for about ½ hour. The solvent is removed and the residue taken up in an organic solvent such as an ether, treated with a dialkyl formamide and then a 10-fold excess of oxalyl chloride. This is all effected at a reduced temperature between about −10° and +10° C. The last mentioned solution is then stirred at the reduced temperature for 1-4 hours, preferably 2 hours. Removing the solvent leaves a residue which is taken up in an inert solvent such as benzene, cooled to about 0° C. and treated with concentrated ammonium hydroxide. The resulting mixture is stirred at a reduced temperature for 1-4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alkyl halides under Williamson reaction conditions (March, Ibid, pg. 357) gives the corresponding ethers.

Aldehydes can be prepared from the corresponding primary alcohols using mild oxidizing agents such as pyridinium dichromate in methylene chloride (Corey, E. J., Schmidt, G., Tet. Lett., 399, 1979), or dimethyl sulfoxide/oxalyl chloride in methylene chloride (Omura, K., Swern, D. Tetrahedron, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds where B is —$CH_3$ are prepared from the corresponding halo-heterocyclic entity preferably where the halogen is I. This haloheterocyclic compound is reacted with the ethynyl zinc chloride entity as described in Reaction Scheme I and more specifically in Example 3. Halo-substituted heterocyclic compounds where B is —$CH_3$ are commercially available or can be prepared by methods in the literature.

The following Examples are set out to illustrate the the invention, not to limit its scope.

EXAMPLE 1

1-(2',6',6'-Trimethylcyclohex-1'-enyl)but-1-ene-3-yne

A solution of 12.17 g (120.27 mmol) diisopropylamine in 200 ml dry tetrahydrofuran was cooled to −78° C. under argon and treated dropwise via syringe with 75 ml of 1.6M (120 mmol) n-butyllithium in hexane. This mixture was stirred at about −78° C. for 1 hour and then treated via cannula with a cooled (−78° C.) solution of 21.99 g (114.35 mmol) β-ionone (1) in 20 ml of dry tetrahydrofuran. This mixture was stirred at about −78° C. for 1 hour, treated dropwise with 21.73 g (125.93 mmol) of diethyl chlorophosphate and allowed to warm to room temperature over 2 hours. This solution was then transferred by cannula to a solution of lithium diisopropylamide prepared by stirring under argon, a solution of 26.57 g (262.57 mmol) diisopropylamine in 150 ml dry tetrahydrofuran and 164 ml of 1.6M (262.4 mmol) n-butyllithium in hexane for 0.5 hour at −78° C. The mixture was allowed to warm to room temperature, stirred for 15 hours, acidified with 250 ml 3N HCl and extracted with pentane. The organic extract was washed for 1N HCl, water, saturated NaHCO$_3$ and saturated NaCl and dried (MgSO$_4$). The product was concentrated and kugelrohr distilled (50° C.; 0.1 mm) to give the captioned compound as a colorles oil.

PMR (CDCl$_3$): δ 1.0 (2CH$_3$, s), 1.45 (2H, m), 1.65 (CH$_3$, s), 1.92 (2H, m) 2.85 (1H, d, J∼3 Hz), 5.35 (1H, dd, J∼16 Hz, 3 Hz), 6.6 (1H, d, J∼16 Hz).

EXAMPLE 2

Ethyl 6-chloronicotinoate

A mixture of 15.75 g (0.1 mol) 6-chloronicotinic acid, 6.9 g (0.15 mol) ethanol, 22.7 g (0.11 mol) dicyclohexylcarbodiimide and 3.7 g dimethylaminopyridine, (0.03 mol), in 200 ml of methylene chloride was heated at reflux for 2 hours. The mixture was allowed to cool, solvent removed in vacuo and residue subjected to flash chromatography to give 16.7 g of the captioned compound as a low-melting white solid.

PMR (CDCl$_3$): δ 1.44 (3H, t, J~6.2 Hz), 4.44 (2H, q, J~4.4 Hz), 7.44 (1H, d, J~8.1 Hz), 8.27 (1H, dd, J~8.1 Hz, 3 Hz), 9.02 (1H, d, j~3 Hz)

EXAMPLE 3

Ethyl 6-[4'-(2'',6'',6''-trimethylcyclohex-1''-enyl)-but-3'-ene-1'-ynyl]nicotinoate Reaction vessels used in this procedure were flame dried under vacuum and all operations carried out in an oxygen-free argon or nitrogen atmosphere. To a solution of the Example 1 compound, 620.7 mg (3.5614 mmol), in 4 ml dry tetrahydrofuran at 0° C. was added dropwise 2.25 ml of 1.6M (3.6 mmol) n-butyllithinum in hexane. This mixture was stirred at 0° C. for 10 minutes at room temperature for 10 minutes and cooled again to 0° C. To this was added, via cannula, a solution of 500 mg (3.6689 mmol) fused zinc chloride in 4 ml dry tetrahydrofuran with stirring at 0° C. for 1 hour and at room temperature for 10 minutes. A solution of 664 mg (3.5774 mmol) ethyl 6-chloronicotinoate in 4 ml of dry tetrahydrofuran was transferred by cannula into a suspension of 430 mg (0.3721 mmol) tetrakis(triphenylphosphine)palladium in 6 ml of dry tetrahydrofuran and stirred for 10 minutes. This mixture was then treated via cannula with the solution of alkynyl zinc and the resultant mixture stirred at room temperature for 60 hours. Water was added (100 ml) and the products extracted with 3×100 ml ether. Combined ether extracts were washed with saturated NaCl solution, dried (MgSO$_4$) and concentrated to give a brown oil. This oil was purified by flash chromatography (silica gel; 10% ethyl acetate in hexanes) followed by high pressure liquid chromatography (Waters 6000; Partisil M-9 10/50; 5% ethyl acetate in hexanes) to give the title compound as a pale yellow oil.

PMR (CDCl$_3$); δ 1.06 (2CH$_3$, s), 1.42 (3H, t, J~7 Hz), 1.46 (2H, m), 1.61 (2H, m), 1.78 (CH$_3$, s) 2.05 (2H, m), 4.42 (2H, t, J~7 Hz), 5.75 (1H, d, J~16.5 Hz), 6.89 (1H, d, J~16.5 Hz), 7.48 (1H, d, J~7.8 Hz), 8.25 (1H, dd, J~7.8, ~2 Hz), 9.15 (1H, d, J~2 Hz).

Proceeding in a similar manner, but substituting for the ethyl 6-chloronicotinoate, the appropriate halo-substituted heterocyclic ester, the following compounds may be prepared:

ethyl 2-[2'-(4''-(2''',6''',6'''-trimethylcyclohex-1'''-enyl)-but-3''-en-1''-ynyl)-5'-pyridinyl]acetate;
ethyl 3-[2'-(4''-(2''',6''',6'''-trimethylcyclohex-1'''-enyl)-but-3''-en-1''-ynyl)-5'-pyridinyl]propionate;
ethyl 4-[2'-(4''-(2''',6''',6'''-trimethylcyclohex-1'''-enyl)-but-3''-en-1''-ynyl)-5'-pyridinyl]butanoate; and
ethyl 5-[2'-(4''-(2''',6''',6'''-timethylcyclohex-1'''-enyl)-but-3''-en-1''-ynyl)-5'-pyridinyl]pentanoate.

EXAMPLE 4

Ethyl 5-bromo-2-furoate

To a stirred suspension of 8.43 g (44.14 mmol) of 5-bromo-2-furoic acid in 100 ml absolute ethanol was added 4 ml of thionyl chloride. This mixture was stirred at reflux for 3 hours and at room temperature for 18 hours. The solvent was removed in vacuo, the residual oil treated with 100 ml water and extracted with 3×75 ml ether. The combined ether extracts were washed with saturated NaHCO$_3$ and saturated NaCl solutions and dried (MgSO$_4$). Solvent was removed in vacuo and the residue kugelrohr distilled (60° C.; 0.4 mm) to give the captioned compound as a colorless oil.

PMR (CDCl$_3$); δ 1.35 (3H, t, J~7 Hz), 4.37 (2H, q, J~7 Hz), 6.45 (1H, d, J~4 Hz), 7.1 (1H, d, J~4 Hz).

EXAMPLE 5

Ethyl 5-bromothiophene-2-carboxylate

To 1.092 g (5.7157 mmol) of 5-bromothiophene-2-carboxaldehyde was added sequentially, 1.507 g (30.75 mmol) sodium cyanide, 60 ml ethanol, 602.5 mg (10.04 mmol) of acetic acid and 10.62 g (122.16 mmol) of manganese dioxide. This mixture was stirred at room temperature for 24 hours, then filtered through celite and the residue washed several times with ether. The combined filtrates were concentrated, then the residue taken up in water and extracted with 3×75 ml ether. Combined ether extracts were washed with saturated NaHCO$_3$, saturated NaCl, dried (MgSO$_4$), concentrated in vacuo and kugelrohr distilled (70° C.; 0.1 mm) to give the captioned compound as a pale yellow oil.

PMR (CDCl$_3$): δ 1.3 (3H, t, J~7 Hz), 4.35 (2H, t, J~7 Hz), 7.12 (1H, d, J~4 Hz), 7.6 (1H, d, J~4 Hz).

EXAMPLE 6

Ethyl 5-[4'-(2'',6'',6''-trimethyl-cyclohex-1''-enyl)-but-3'-en-1'-ynyl]-2-furoate Ethyl 5-[4'-(2'',6'',6''-trimethyl-cyclohex-1''-enyl)-but-3'-en-1'-ynyl]thiophene-2-carboxylate Employing the procedure and conditions described in Example 3, but using instead the ethyl 5-bromo-2-furoate prepared in Example 4 or the ethyl 5-bromo-thiophene-2-carboxylate prepared in Example 5, respectively, the title compounds were prepared. The furoate had the following PMR spectral characteristics:

PMR (CDCl$_3$): δ 1.1 (6H, s), 1.43(3H, t, J~7.6 Hz), 1.52 (2H, m), 1.65 (2H, m), 1.81 (3H, ə), 2.1(2H, m), 4.42 (2H, q, J~7.6 Hz), 5.73 (1H, d, J~16.8 Hz), 6.66 (1H, d, J~3.5 Hz), 6.83 (1H, d, J~16.8 Hz), 7.21 (1H, d, J~3.5 Hz).

The thiophene-2-carboxylate compound had the following PMR spectral characteristics:

PMR (CDCL$_3$): δ 1:08(6H, s), 1.39 (3H, t, J~7.2 Hz), 1.50 (2H, m), 1.62 (2H, m), 1.79 (3H, s), 2.08 (2H, m), 4.37 (2H, q, J~7.5 Hz), 5.72 (1H, d, J~16.5 Hz), 6.76 (1H, d, J~16.5 Hz), 7.14 (1H, d, J~3.9 Hz), 7.67 (1H, d, J~3.9 Hz).

Proceeding in a similar manner, but substituting for the ethyl thiophene-2-carboxylate and the ethyl 5-bromo-2-furoate, the appropriate heterocyclic ester, the following compounds may be prepared:

ethyl 2-[5'-(4''-(2''',6''',6'''-trimethylcyclohexenyl)-but-3''-en-1''-ynyl)-2'-furyl]acetate;
ethyl 3-[5'-(4''-(2''',6''',6'''-trimethylcyclohex-1'''-enyl)-but-3''-en-1''-ynyl)-2'-furyl]propionate;
ethyl 4-[5'-(4''-(2''',6''',6'''-trimethylcyclohex-1'''-enyl)-but-3''-en-1''-ynyl)-2'-furyl]butanoate;
ethyl 5-[5'-(4''-(2''',6''',6'''-trimethylcyclohex-1'''-enyl)-but-3''-en-1''-ynyl)-2'-furyl]pentanoate;
ethyl 2-[5'-(4''-(2''',6''',6'''-trimethylcyclohex-1'''-enyl)-but-3''-en-1''-ynyl)-2'-thiophenyl]acetate;
ethyl 3-[5'-(4''-(2''',6''',6'''-trimethylcyclohex-1'''-enyl)-but-3''-en-1''-ynyl)-2'-thiophenyl]propionate;
ethyl 4-[5'-(4''-(2''',6''',6'''-trimethylcyclohex-1'''-enyl)-but-3''-en-1''-ynyl)-2-thiophenyl]butanote; and ethyl 5-[5'-(4'''-(2'''',6'''',6''''-trimethylcyclohex-1''''-enyl)-but-3'''-en-1'''-ynyl)-2'-thiophenyl]pentanoate.

EXAMPLE 7

6-[4'-(2'',6'',6''-Trimethylcyclohex-1''-enyl)-but-3'-en-1'-ynyl]nicotinic acid

Nitrogen gas was bubbled through the solutions used in this experiment immediately before use. To a stirred solution of 53 mg (0.1641 mmol) ethyl 6-[4'-(2'',6'',6''-trimethyl cyclohex-1''-enyl)but-3'-ene-1'-ynyl]nicotinoate in 200 ml ethanol was added under nitrogen 132 ml of a 1.86M (0.2459 mmol) solution of KOH in ethanol and water. After being stirred at room temperature for 3 hours, solvent was removed in vacuo and the residue treated with 1 ml water and extracted with 2×1 ml portions of ether. The aqueous layer was then acidified with 50% aqueous acetic acid and extracted with 3×2 ml ether. Combined ether extracts were dried ($MgSO_4$) and concentrated in vacuo to give the title product as a pale yellow powder.

PMR ($CDCl_3$): δ 1.06 (6H, s), 1.48 (2H, m), 1.62 (2H, m), 1.78 (3H, s), 2.05 (2H, m), 5.75 (1H, d, J~16.4 Hz), 6.93 (1H, d, J~16.4 Hz), 7.55 (1H, d, J~8.1 Hz), 8.35 (1H, dd, J~8.1, 2.3 Hz), 9.29 (1H, d, J~2.3 Hz).

Proceeding in a similar manner, esters prepared according to Example 6 may be converted to the corresponding acid. For example:

5-[4'-(2'',6'',6''-trimethyl-cyclohex-1''-enyl)-but-3'-en-1'-ynyl]furanoic acid; and 5-[4'-(2'',6'',6''-trimethylcyclohex-1''-enyl)-but-3'-en-1'-ynyl]thiophen-2-carboxylic acid.

EXAMPLE 8

2-[4'-(2'',6'',6''-Trimethylcyclohex-1''-enyl)-but-3'-ene-1'-ynyl]-5-hydroxymethylpyridine A 250 ml 3-necked flask is fitted with a stirrer, a dropping funnel, a nitrogen inlet and a thermometer. In the flask is placed a solution of 379.5 mg (10 mmol) of lithium aluminum hydride in 30 ml of dry diethyl ether. The solution is cooled to −65° C. under nitrogen and a solution of 3.2343 g (10 mmol) of ethyl 6-[4'-(2'',6'',6''-trimethylcyclohex-1''-enyl)-but-3'-ene-1'-ynyl]-nicotinoate in 15 ml of dry ether is added dropwise at a rate such that the temperature does not exceed −60° C. The mixture is stirred at −30° C. for 1 hour and the excess hydride is then destroyed by the addition of 300 mg (3.4 mmol) of ethyl acetate. The reaction mixture is then hydrolyzed by adding 3 ml of saturated ammonium chloride solution and allowing the temperature to rise to room temperature. The mixture is then filtered and the residue washed with ether. The ether layer is then washed with saturated sodium chloride solution, dried ($MgSO_4$) and then concentrated in vacuo. The residue is purified by chromatography followed by recrystalliztion to give the title compound.

EXAMPLE 9

2-[4'-(2'',6'',6''-trimethylcyclohex-1''-enyl)-but-3'-ene-1'-ynyl]-5-acetoxymethylpyridine A solution of 2.81 g (10 mmol) of 2-[4'-(2'',6'',6''-trimethylcyclohex-1''-enyl)-but-3'-ene-1'-ynyl]-5-hydroxymethylpyridine, 600 mg (10 mmol) of glacial acetic acid, 2.06 g (10 mmol) of dicyclohexylcarbodiimide and 460 mg (3.765 mmol) of 4-dimethylaminopyridine in 150 ml methylene chloride is stirred at room temperature for 48 hours. The reaction mixture is then filtered and the residue washed with 50 ml of methylene chloride. The filtrate is then concentrated in vacuo and the residue is purified by chromatography followed by recrystallation to give the title compound.

By the same process, any of the acids or esters prepared in Examples 3 and 6 above may be converted to their corresponding primary alcohol analog.

EXAMPLE 10

2-[4'-(2'',6'',6''-trimethylcyclohex-1''-enyl)-but-3'-ene-1'-ynyl]-pyridine-5-carboxaldehyde A solution of 1.396 g (11 mmol) of freshly distilled oxalyl chloride in 25 ml of methylene chloride is placed in a 4-necked flask equipped with a stirrer, a thermometer and two pressure-equalizing addition funnels fitted with drying tubes. The solution is cooled to −60° C. and then treated dropwise with a solution of 1.875 g (24 mmol) of dimethyl sulfoxide (distilled from calcium hydride) in 5 ml of methylene chloride over a five minute period. The reaction mixture is then stirred at −60° C. for an additional 10 minutes. A solution of 2.81 g (10 mmol) of 2-[4'-(2'',6'',6''-trimethylcyclohex-1''-enyl)-but-3'-ene-1'-ynyl]-5-hydroxymethylpyridine in 10 ml of methylene chloride is then added to the reaction mixture over a period of 5 minutes. The mixture is stirred for a further 15 minutes and is then treated with 5.06 g (50 mmol) of triethylamine. The cooling bath is then removed and the mixture is allowed to warm to room temperature. Thirty ml of water is then added to the mixture and stirring is continued for a further 10 minutes. The organic layer is then separated and the aqueous layer is extracted with 20 ml of methylene chloride. The organic layers are then combined and washed successively with dilute HCl, water and dilute $Na_2CO_3$ solution and then dried ($MgSO_4$). The solution is then filtered and concentrated in vacuo and the residue is purified by chromatography followed by recrystallization to give the title compound.

All alcohols prepared in Example 9 may be oxidized to their corresponding aldehyde by this method.

EXAMPLE 11

2-[4'-(2'',6'',6''-trimethylcyclohex-1''-enyl)-but-3'-ene-1'-ynyl]-5-(1''-hydroxypropyl)pyridine Four ml of a 3M (12 mmol) solution of ethylmagnesium bromide in ether is placed in a 3-necked flask fitted with a mechanical stirrer, a reflux condenser protected by a drying tube and a pressure-equalizing dropping funnel protected by a drying tube. The flask is cooled in an ice-bath nd a solution of 2.8 g (10 mmol) of 2-[4'-(2'',6'',6''-trimethylcyclohex-1''-enyl)-but-3'-ene-1'-ynyl]-pyridine-5-carboxaldehyde in 10 ml of dry ether is added slowly with vigorous stirring. The cooling bath is then removed and the mixture heated at reflux for 3 hours. The mixture is then cooled in an ice-salt bath and 5 ml of saturated ammonium chloride solution is added. The mixture is stirred for a further 1 hour and then filtered and the residue washed with two 10 ml portions of ether. The ether solution is then separated, dried ($MgSO_4$) and the ether removed in vacuo. The residue is then purified by chromatography followed by recrystallization to give the title compound.

Using the same procedure, but substituting for the pyridine compound noted above, any of the other heteroaromatic aldehydes prepared as per Example 10 can be converted to a secondary alcohol.

Such secondary alcohols may be converted to their corresponding ketone using the same reagents in approximately the same relative amounts of reagent to reactant and essentially the same conditions described in Example 10.

EXAMPLE 12

2-[4'-(2'',6'',6''-trimethylcyclohex-1''-enyl)-but-3'-ene-1'-ynyl]-5-dimethoxymethylpyridine A round-bottomed flask is fitted with a Dean-Stark apparatus under a reflux condenser protected by a drying tube. A mixture of 3.35 g (12 mmol) of 2-[4'-(2'',6'',6''-trimethylcyclohex-1''-enyl)-but-3'-ene-1'-ynyl]pyridine-5-carboxaldehyde, 4.80 mg (15 mmol) of anhydrous methanol, 2 mg of p-toluenesulfonic acid monohydrate and 10 ml of anhydrous benzene is placed in the flask and the mixture heated at reflux under nitrogen until close to the theoretical amount of water is collected in the Dean-Stark trap. The reaction mixture is cooled to room temperature and extracted successively with 5 ml of 10% sodium hydroxide solution and two 5 ml portions of water and then dried (MgSO$_4$). The solution is then filtered and the solvent removed in vacuo. The residue is purified by chromatography and then recrystalliztion to give the title compound.

In a similar manner, any aldehyde or ketone of any heteroaromatic containing compound made as per Examples 10 and 11 may be converted to an acetal or a ketal.

What is claimed is:

1. A compound of the formula

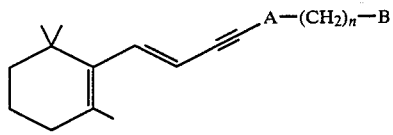

where
  A is pyridyl;
  n is 0-5; and
  B is H, —COOH or its esters of saturated aliphatic alcohols of ten or fewer carbon atoms, or the cyclic or saturated aliphatic cyclic alcohols of 5 to 10 carbon atoms, phenol, amides or mono- or di-substituted amides of saturated aliphatic alcohols of ten or fewer carbon atoms, or the cyclic or saturated aliphatic cyclic radicals of 5 to 10 carbon atoms, and pharmaceutically acceptable salts, —CHO and its lower alkyl acetal derivatives, —CH$_2$OH and its lower alkyl ethers and acyl esters of saturated aliphatic acids of ten or fewer carbon atoms or the cyclic or saturated aliphatic cyclic acids of 5 to 10 carbon atoms, and benzoic acid, or —COR$_1$ and its lower alkyl ketal derivatives where R$_1$ is —(CH$_2$)$_n$CH$_3$ where n is define above; or a pharmaceutically acceptable salt.

2. A compound of claim 1 where B is —COOH and its esters, —CHO or —CH$_2$OH, or a pharmaceutically acceptable salt.

3. A compound according to claim 1 where n is 0 which is
  ethyl 6-[4'-(2'',6'',6''-trimethylcyclohex-1''-enyl)-but-3'-en-1'-ynyl]nicotinoate; or
  6-[4'-(2'',6'',6''-trimethylcyclohex-1''-enyl)-but-3'-en-1'-ynyl]nicotinic acid or a pharmaceutically acceptable salt thereof.

4. A method for treating psoriasis in a mammal which method comprises administering to a mammal in need thereof, a therapeutically effective amount of a compound of the formula I alone or in admixture with a pharmaceutically accepptble excipient where formula I is

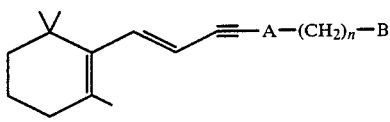

wherein A is pyridyl, n is 0-5; and B is H, —COOH and its esters, amides and pharmaceutically acceptable salts, —CHO and its acetal derivatives, or —COR$_1$ and its ketal derivatives where R$_1$ is —(CH$_2$)$_n$CH$_3$ where n is defined above; or a pharmaceutically acceptable salt.

5. A pharmaceutical composition comprising a pharmaceutically acceptable excipient and a compound of the formula

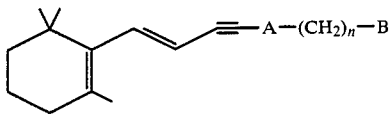

wherein A is pyridyl, furyl, thienyl, pyridazinyl, pyrimidinyl or pyrazinyl; n is 0-5; and B is H, —COOH and its esters, amides and pharmaceutically acceptable salts, —CHO and its acetal derivatives, or —COR$_1$ and its ketal derivatives where R$_1$ is —(CH$_2$)$_n$CH$_3$ where n is defined above; or a pharmaceutically acceptable salt.

* * * * *